United States Patent [19]

N'Guyen et al.

[11] Patent Number: 5,114,716
[45] Date of Patent: May 19, 1992

[54] ANTI-OXIDANT SYSTEM CONTAINING STABILIZED ASCORBYL ESTER, TOCOPHEROL OR CAFEIC ACID OR A DERIVATIVE THEREOF, A COMPLEXING AGENT AND A POLYPEPTIDE, AND COMPOSITIONS CONTAINING THE ANTI-OXIDANT SYSTEM

[75] Inventors: Quang L. N'Guyen, Antony; Jacqueline Griat, Ablon; François Millecamps, Paris; Gérard Lang, Saint-Gratien; Serge Forestier, Claye Souilly, all of France

[73] Assignee: Societe Anonyme Dite: L'Oreal, Paris, France

[21] Appl. No.: 385,878

[22] Filed: Jul. 28, 1989

[30] Foreign Application Priority Data

Jul. 29, 1988 [FR] France ............................... 88 10295

[51] Int. Cl.$^5$ .............................................. A61K 7/00
[52] U.S. Cl. ...................................... 424/401; 424/59; 424/60; 424/65; 424/70; 424/76.1; 514/2; 514/458; 514/474; 514/555; 514/844; 252/397
[58] Field of Search ............................ 424/401, 59-65, 424/69, DIG. 6; 514/844-848, 458, 474, 555, 844; 252/397

[56] References Cited

U.S. PATENT DOCUMENTS

| | | | |
|---|---|---|---|
| 2,383,815 | 8/1945 | Riemenschneider et al. | 260/398.5 |
| 2,462,663 | 2/1949 | Norris | 99/163 |
| 4,369,180 | 1/1983 | Mihalovits | 424/177 |
| 4,424,234 | 1/1984 | Alderson et al. | 424/45 |
| 4,847,069 | 7/1989 | Bissett et al. | 424/63 |
| 4,847,071 | 7/1989 | Bissett et al. | 424/63 |
| 4,906,460 | 3/1990 | Kim et al. | 424/72 |

FOREIGN PATENT DOCUMENTS

| | | |
|---|---|---|
| 1081233 | 8/1967 | United Kingdom . |
| 1193027 | 5/1970 | United Kingdom . |
| 1370303 | 4/1974 | United Kingdom . |

OTHER PUBLICATIONS

Journal of Food Science, vol. 51, No. 5, 1986, pp. 1293-1296, J. R. Mahoney, Jr. "Role of alpha-Tocopherol, Ascorbic acid, citric acid and EDTA as oxidants in model systems". Search Report of FR 88 10295.

Primary Examiner—Thurman K. Page
Assistant Examiner—G. S. Kishore
Attorney, Agent, or Firm—Cushman, Darby & Cushman

[57] ABSTRACT

An anti-oxidant system contains, in combination, at least one stabilized ascorbyl ester, at least one tocopherol or a mixture of tocopherols, or cafeic acid or a derivative thereof, at least one complexing agent and at least one non-thiol polypeptide. The anti-oxidant system is employed to stabilize fatty bodies and cosmetic compositions.

19 Claims, No Drawings

ANTI-OXIDANT SYSTEM CONTAINING STABILIZED ASCORBYL ESTER, TOCOPHEROL OR CAFEIC ACID OR A DERIVATIVE THEREOF, A COMPLEXING AGENT AND A POLYPEPTIDE, AND COMPOSITIONS CONTAINING THE ANTI-OXIDANT SYSTEM

BACKGROUND OF THE INVENTION

The present invention relates to a new anti-oxidant system based on a stabilized ascorbyl ester, containing, in combination therewith, at least one tocopherol or a mixture of tocopherols or cafeic acid or one of its derivatives, at least one complexing agent and at least one polypeptide, to the use of such an anti-oxidant system and to compositions based on oleaginous materials containing such a system, and principally cosmetic compositions.

It is known that fatty bodies have a tendency to be oxidized, even at ambient temperature and this oxidation (or rancidness) makes them acquire new properties, principally of taste or smell, which are generally considered as undesirable when these fatty bodies are incorporated, for example, in food compositions or in cosmetic compositions.

There are currently employed, in compositions containing fatty bodies or materials, protective agents which, in fact, play the role of an anti-oxidant.

Among known anti-oxidants, ascorbic acid is currently used which acts principally by direct absorption of oxygen. However, ascorbic acid is only very slightly soluble in fatty bodies and it is consequently difficult to use in order to protect the fatty material against oxidation.

In order to solubilize the ascorbic acid molecule in fatty materials, it has been proposed to use various ascorbyl esters such as, for example, ascorbyl stearate, palmitate or laurate; see for example, the article of C. F. Bourgeois, "Revue Francaise des Corps Gras", No. 9, pages 353-356 (September 1981).

It is also known, apart from their own anti-oxidant properties, that ascorbic derivatives also have the property of improving the activity of anti-oxidant agents such as tocopherols or cafeic acid and its esters, by favoring the regeneration of these anti-oxidant agents; see for example H. S. Olcott, "Oil Soap", 18, (1941), 77 and U.S. Pat. No. 2,462,663.

Various improvements of these binary anti-oxidant agents, of the ascorbic derivatives + tocopherols or ascorbic derivatives + cafeic derivatives types have been proposed, by providing for the addition of a third constituent which again improves anti-oxidant effects. Among the third constituents of these ternary systems, there can be mentioned, principally, p-aminobenzoic acid (U.S. Pat. No. 2,462,633), phospholipids (R. W. Riemenschneider et al, "Oil Soap"—1941, 47) and amines (Klaui, "The Functional (Technical) Uses of Vitamins", ed. by M. Stein, University of Nottingham Seminar Vitamins, London, England, 1971, page 110).

It has now been discovered that it is possible to improve considerably the anti-oxidant properties of ascorbyl esters by employing these anti-oxidants conjointly with at least one tocopherol or a mixture of tocopherols or cafeic acid or one of its derivatives, at least one complexing agent and at least one non-thiol polypeptide. A significant synergistic effect has been observed.

The present invention thus relates to a new anti-oxidant system, free from a reducing agent compound, comprising at least one stabilized ascorbyl ester, at least one tocopherol or a mixture of tocopherols or cafeic acid or one of its derivatives, at least one complexing agent and at least on non-thiol polypeptide.

The ascorbyl ester is indeed an ester soluble in the fatty body and in particular is an ester of an aliphatic acid having 6-24 carbon atoms such as, for example, ascorbyl stearate, palmitate or laurate.

By "tocopherols" is meant not only $\alpha$- tocopherols, but also $\beta$-, $\gamma$- or $\delta$-tocopherol, as well as mixtures thereof.

The cafeic acid derivatives are either esters or amides of this acid.

Representative esters of cafeic acid include, principally, the alkyl esters such as methyl, ethyl or butyl esters, or the phytol ester.

Representative amides of cafeic acid include, principally, the N-alkyl amides, such as N-octyl amide.

By a complexing agent is meant a compound which is capable of inhibiting, by chelation, the catalytic effect of the transition metals to the free state in the medium.

Representative useful complexing agents include, principally, ethylenediamine tetraacetic acid (EDTA), the pentasodium salt of diethylenetriamine pentaacetic acid (DTPA), hexadecylamine salicylate (HDAS), citric acid, tartaric acid or its sodium salt, phytic acid, dibenzyldithiocarbamate and derivatives of polyphosphonic acid, or a mixture of such agents.

Representative derivatives of polyphosphonic acid and their salts include, principally, alkylenediamino poly (methylene phosphonic) acids and principally products sold by Monsanto under the trade names DEQUEST 2041 (ethylenediamine tetra (methylene phosphonic) acid), DEQUEST 2046 (the pentasodium salt of DEQUEST 2041), DEQUEST 2051 (hexamethylene tetra (methylene phosphonic) acid), DEQUEST 2054 (the hexapotassium salt of DEQUEST 2051), DEQUEST 2060S (diethylenediamine penta (methylene phosphonic) acid) and DEQUEST 2066 (the heptasodium salt of DEQUEST 2060S).

In addition to the at least one complexing agent listed above, the composition in accordance with the present invention can also contain a secondary complexing agent, such as sorbitol.

The non-thiol polypeptide of the anti-oxidant system in accordance with the present invention has an average molecular weight ranging from about 1,000 to about 100,000. Representative polypeptides, that can be employed, include, in particular, the following:

(a) the polypeptide sold by Croda Chemicals Ltd. under the tradename "KERASOL" (soluble keratin polypeptide having an average molecular weight of about 100,000), (b) the polypeptide sold by Societe Naarden under the tradename "Polypeptide SF" (partially neutralized animal collagen polypeptide having an average molecular weight of about 1,000), (c) the polypeptide sold by Societe Naarden under the tradename "Polypeptide LSN" (animal collagen polypeptide in the form of the ammonium salt containing about 3% (max) of inorganic salt), and (d) the polypeptide sold by Laboratoires Serobiologiques de Nancy under the tradename "LACTOLAN" (polypeptide obtained starting with previously delipidated fresh cow milk.

The ascorbyl ester is generally present in the four constituent containing anti-oxidant system of the present invention in an amount ranging from 5 to 70 weight percent.

It has been noted in a quite surprising fashion that, in such combinations, the anti-oxidant activity of the tocopherols and cafeic acid, resulted in a significant synergistic effect with the ascorbyl ester, in the presence of the complexing agent—non-thiol polypeptide couple.

In accordance with the present invention, the anti-oxidant system preferably comprises:
0.5 to 20 weight percent tocopherol(s) or cafeic acid (or one of its esters or amides).
5 to 70 weight percent ascorbyl ester,
2 to 20 weight percent complexing agent and
1 to 80 weight percent non-thiol polypeptide.

The molar ratio of ascorbyl ester to the tocopherol(s) or cafeic acid or one of its esters or amides must be, preferably, greater than or equal to 3.

The present invention also relates to compositions containing fatty bodies or materials and at least one anti-oxidant system such as defined above.

The compositions of the present invention can be, principally, food composition (comestible oils, lard, butter, margarine or other butter substitutes) or cosmetic compositions.

The fatty bodies present in the cosmetic compositions of the invention are, for example, fatty bodies of animal origin such as cetin (spermaceti), beeswax, lanolin, perhydrosqualene, turtle oil and the like; vegetable fatty bodies in the form of oils, fats or waxes, such as sweet almond oil, avocado oil, olive oil and the like; hydrogenated copra or cabbage palm oil, cocoa butter, Carnauba wax, Montana wax; as well as synthetic oils constituted by esters and/or ethers of glycerol or glycol such as, for example, those described in French patents Nos. 75.24656, 75.24657, and 75.24658.

In addition to the more or less oxidizable fatty bodies, the cosmetic compositions can contain products sensitive to oxidation such as, for example, vitamin F or β-carotene.

The cosmetic compositions according to the present invention are provided in the form of oily solutions, emulsions, solid products, lotions or also micro-dispersions, and ionic or non-ionic lipid vesicles. These compositions constitute principally milks for the care of the skin, creams (face creams, hand creams, body creams, anti-solar creams, make-up remover creams, foundation creams), foundation fluids, make-up remover milks, anti-solar milks, bath oils, lip rouge, eyelid make-up, deodorant sticks and the like.

In accordance with a preferred embodiment of the present invention, the cosmetic compositions are provided in the form of creams intended for the protection against the oxidation of the lipids of the skin.

In the cosmetic compositions according to the present invention, the anti-oxidant system, such as defined above, is generally present so that the following proportions relative to the total weight of the composition are established:

| | |
|---|---|
| Tocopherol(s) or cafeic acid (or one of its esters or amides) | 0.05 to 0.5 wt % |
| Ascorbyl ester | 0.45 to 1.6 wt % |
| Complexing agent | 0.2 to 0.5 wt % |
| Polypeptide (active material) | 0.05 to 8 wt % |

The compositions of the present invention can also contain active compounds or ingredients, employed in a usual manner in the compositions mentioned above, such as surface-active agents, dyes, perfumes, astringent-products, products absorbing ultra-violet rays, organic solvents, water and the like.

These compositions are prepared in accordance with conventional methods.

There are now given, as an illustration, several examples of anti-oxidant systems in accordance with the present invention, as well as several examples of cosmetic compositions containing such anti-oxidant systems.

EXAMPLE 1

| | |
|---|---|
| Tocopherols (mixture of α-, β-, γ- and δ-tocopherol) | 5 wt % |
| Ascorbyl palmitate | 65 wt % |
| EDTA | 5 wt % |
| Polypeptide, "Polypeptide SF" (active material) | 25 wt % |

EXAMPLE 2

| | |
|---|---|
| Cafeic acid | 20 wt % |
| Ascorbyl palmitate | 50 wt % |
| Citric acid | 10 wt % |
| Sorbitol | 10 wt % |
| Polypeptide, "Kerasol" (active material) | 10 wt % |

EXAMPLE 3

| | |
|---|---|
| Methyl ester of cafeic acid | 13 wt % |
| Ascorbyl palmitate | 10 wt % |
| DPTA | 12 wt % |
| Polypeptide, "Polypeptide LSN" (active material) | 65 wt % |

Examples of Cosmetic Compositions

| | |
|---|---|
| I  Anhydrous balm | |
| Karite oil | 60 wt % |
| Turnsole oil | 20 wt % |
| Vitamin F | 2 wt % |
| Soy lecithin | 4.9 wt % |
| Tocopherols | 0.45 wt % |
| Ascorbyl palmitate | 1.6 wt % |
| Citric acid | 0.10 wt % |
| EDTA | 2 wt % |
| Polypeptide, "LACTOLAN", (active material) | 1 wt % |
| Petrolatum, sufficient amount for | 100 weight percent |
| II  Oil-in-water emulsion care cream | |
| Sorbitan monostearate oxyethylenated with 20 moles of ethylene oxide, Tween 60 | 1 wt % |
| Glycerol stearate | 2 wt % |
| Stearic acid | 1.4 wt % |
| Triethanolamine | 0.7 wt % |
| Cetyl alcohol | 0.5 wt % |
| Turnsole oil | 15 wt % |
| Vitamin F | 2 wt % |
| Ascorbic acid | 1 wt % |
| Soy lecithin | 0.6 wt % |
| Petrolatum oil | 2.4 wt % |
| Cafeic acid | 0.1 wt % |
| Ascorbyl palmitate | 0.6 wt % |
| DTPA | 0.5 wt % |
| Polypeptide - "Polypeptide LSN" (active material) | 7 wt % |
| Carboxyvinyl polymer, sold under the tradename "Carbopol 940" | 0.2 wt % |

-continued

| | |
|---|---|
| by Goodrich | |
| Triethanolamine | 0.2 wt % |
| Perfume | 0.8 wt % |
| Preservative - methylparahydroxy-benzoate | 0.25 wt % |
| Water, sufficient amount for | 100 wt percent |

III—Gel for the care of the face in the form of vesicle dispersion

1st stage: An aqueous dispersion of lipid spherules is prepared in accordance with the method in French patent No. 75.20456 (2.315.991) starting with the following materials:

non-ionic amphiphile lipid having the formula:

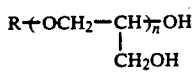

wherein

R is hexadecyl and n has an average statistical value equal to 3

| | |
|---|---|
| Cholesterol | 4 g |
| Methylparahydroxybenzoate | 0.3 g |
| Glycerine | 3 g |
| Demineralized water | 42.5 g |

2nd stage: There are added to the dispersion of spherules obtained in the 1st stage, the following substances:

| | |
|---|---|
| Perfume | 0.4 g |
| Corn oil | 18 g |
| Tocopherols (mixture of α-, β-, γ- and δ-tocopherols) | 0.5 g |
| Ascorbyl palmitate | 1 g |
| EDTA | 0.3 g |
| Polypeptide, "Polypeptide SF" (active material) | 5 g |
| Carboxy vinyl polymer, sold under the trade name "Carbopol 940" by Goodrich | 0.4 g |
| Triethanolamine | 0.4 g |
| Demineralized water | 20.2 g |

What is claimed is:

1. An anti-oxidant system consisting essentially of at least one stabilized ascorbyl ester present in an amount ranging from 5-70 weight percent, at least one tocopherol or caferic acid or an ester or an amide there of present in an amount ranging from 0.5 to 20 weight percent, at least one chelating agent present in an amount ranging from 2 to 20 weight percent and at least one non-thiol peptide present in an amount ranging from 1 to 80 weight percent.

2. The anti-oxidant system of claim 1 wherein said ascorbyl ester is an ester of an aliphatic acid having 6-24 carbon atoms.

3. The anti-oxidant system of claim 2 wherein said ascorbyl ester is ascorbyl stearate, ascorbyl palmitate or ascorbyl laurate.

4. The anti-oxidant system of claim 1 wherein said derivative of cafeic acid is an ester or amide thereof.

5. The anti-oxidant system of claim 4 wherein said ester of cafeic acid is the methyl, ethyl, butyl or phytol ester of cafeic acid.

6. The anti-oxidant system of claim 4 wherein said amide of cafeic acid is an N-alkyl amide of cafeic acid.

7. The anti-oxidant system of claim 6 wherein said N-alkyl amide is N-octyl amide of cafeic acid.

8. The anti-oxidant system of claim 1 wherein said chelating agent is selected from the group consisting of ethylenediamine tetraacetic acid, the pentasodium salt of diethylenetriamine pentaacetic acid, hexadecylamine salicylate, citric acid, tartaric acid, sodium tartrate, phytic acid, dibenzyldithiocarbamate, a derivative of polyphosphic acid, and a mixture thereof.

9. The anti-oxidant system of claim 9 wherein said secondary chelating agent is sorbitol.

10. The anti-oxidant system of claim 1 wherein said non-thiol polypeptide has a molecular weight ranging from 1,000 to 100,000.

11. The anti-oxidant system of claim 1 wherein said ascorbyl ester is present in an amount ranging from 5 to 70 weight percent.

12. The anti-oxidant system of claim 1 wherein said chelating agent is present in an amount ranging from 2 to 20 weight percent.

13. The anti-oxidant system of claim 1 wherein said non-thiol polypeptide is present in an amount ranging from 1 to 80 weight percent.

14. The anti-oxidant system of claim 1 wherein the molar ratio of said ascorbyl ester to said tocopherol or cafeic acid or a derivative thereof is greater than or equal to 3.

15. A composition comprising a fatty body and the anti-oxidant system of claim 1.

16. A cosmetic composition comprising a fatty body and the anti-oxidant system of claim 1 wherein said anti-oxidant system consisting essentially of based on the total weight of said composition 0.05 to 0.5 weight percent tocopherol or cafeic acid or an ester or amide thereof, 0.45 to 1.6 weight percent ascorbyl ester, 0.2 to 0.5 weight percent chelating agent and 0.5 to 8 weight percent introduce non-thiol polypeptide.

17. The cosmetic composition of claim 16 wherein said ascorbyl ester is ascorbyl palmitate.

18. The cosmetic composition of claim 16 wherein said chelating agent is selected from the group consisting of ethylenediamine tetracetic acid, citric acid, the pentasodium salt of diethylenetriamine pentaacetic acid, dibenzyldithiocarbamate, a derivative of polyphosphonic acid, and a mixture thereof.

19. The cosmetic composition of claim 16 in the form of a cream for the protection against the oxidation of the lipids of the skin.

* * * * *